United States Patent [19]

Schwartz et al.

[11] 4,147,775

[45] Apr. 3, 1979

[54] ANTISEPTIC COMPOSITION

[76] Inventors: Stephen H. Schwartz, 2001 N. 51 Ave.; Alexander Buchwald, 3130 N. 49 Ave., both of Hollywood, Fla. 33021

[21] Appl. No.: 887,547

[22] Filed: Mar. 17, 1978

Related U.S. Application Data

[63] Continuation of Ser. No. 730,008, Oct. 6, 1976, abandoned.

[51] Int. Cl.$^2$ .............................................. A61K 33/18
[52] U.S. Cl. ...................................................... 424/150
[58] Field of Search ........................................... 424/150

[56] References Cited

U.S. PATENT DOCUMENTS

| 60,753 | 1/1867 | Lennig | 424/150 |
|---|---|---|---|
| 984,106 | 2/1911 | Reed et al. | 424/150 |
| 2,425,285 | 8/1947 | Strickler | 424/150 |
| 2,863,798 | 12/1958 | Shelawski et al. | 424/150 |
| 3,070,496 | 12/1962 | James | 424/150 |
| 3,152,951 | 10/1964 | Perlman | 424/150 |
| 3,542,921 | 11/1970 | Wyatt | 424/150 |

Primary Examiner—Jerome D. Goldberg
Attorney, Agent, or Firm—LeBlanc & Shur

[57] ABSTRACT

A non-irritating antiseptic composition is disclosed. The composition of this invention comprises a combination of magnesium and iodine formulated from Magnesium Usta, resublimated iodine and iodine crystals and powder, which composition is stable in a closed container and suitable for topical application. The composition of this invention may be used alone, or as a bandage impregnate, or may be incorporated in a pharmaceutical or cosmetic vehicle as a general antiseptic, disinfectant, or germicidal agent.

8 Claims, No Drawings

ANTISEPTIC COMPOSITION

This application is a continuation of application Ser. No. 730,008, filed Oct. 6, 1976, and now abandoned.

Tincture of iodine, an antiseptic of known efficacy, has two major disadvantages. Tincture of iodine will stain both skin and fabric, and more importantly, Tincture of iodine is a tissue irritant. While Tincture of iodine is highly effective then as a germicidal agent, its use is limited due to the fact that application to an open wound or even a small scratch will burn or irritate tissue and generally cause a painful reaction.

It has been discovered, however, that the excellent germicidal and antiseptic properties of iodine may be incorporated in a medicinal composition that will not burn or irritate when applied to an open wound or abrasion. Furthermore, the medicinal composition of this invention is stable when maintained in a closed container against sublimation of the iodine component, and therefore it may be stored for extended periods without loss of potency. It has furthermore been discovered that the medicinal composition of this invention may be incorporated in a wide variety of different vehicles such as lotions, ointments or the like for application to boils, varicose-ulcers, cuts, burns, abrasions, blisters and the like. In the alternative, the composition of this invention, which is flesh colored, may be incorporated in cosmetic vehicles such as after-shave, ladies foundation make-up and the like. Topical application thereof then permits the user to take advantage of the germicidal and antiseptic characteristics of iodine, without skin irritation, or staining.

The antiseptic composition of this invention, POWDER-DINE, is formulated by a combination of Magnesium Usta as a major component with resublimated iodine and iodine crystals. After 48 hours approximately, an additional iodine powder is incorporated in the mixture. The composition is then maintained at room temperature in a sealed, covered container an additional 48 hours and subsequently thoroughly shaken thereafter. It is essential to formulation of this invention that no metal containers, stir rods or the like be utilized and that the composition be sealed in an air-tight container.

The composition, however, may be incorporated in for example talc to form a medicated powder, in anhydrous lanolin in white petrolateum or USP grade ointment base to provide an ointment or surgical dressing. In addition, as is noted above, the composition of this invention may be admixed with any standard after-shave lotion or with a make-up stick or cream for the medicated treatment of acne or other skin disorders.

The composition furthermore, in ointment form, may be utilized as a bandage impregnate, or the composition may be dispensed in an aerosol bandage composition, as will be subsequently described, as a wound dressing.

Accordingly, it is an object of this invention to provide a medicinal composition which may be incorporated in a wide variety of vehicles for use by topical application as a germicide or antiseptic.

It is a further object to provide an antiseptic composition utilizing iodine which will not stain the flesh or irritate or burn cuts, wounds, or abrasions.

It is a further object to provide a magnesium-iodine composition which is stable in a closed container and may be dispensed directly as a dry powder on cuts, burns, abrasions and the like, or incorporated as a bandage impregnate or wound dressing in an ointment or aerosol form.

It is yet another object to provide an antiseptic composition which may be incorporated in cosmetic vehicles to provide germicidal properties, but which will not stain, burn or irritate the skin when topically applied.

These and other objects will become readily apparent with reference to the following description:

PREPARATION

The medicinal composition of this invention is prepared from commercially available chemicals as will be subsequently described. In formulating the composition, however, it is essential that metal containers, stir rods, and the like not be used and exposure to air should be minimized. In a preferred method of formulation, a glass container and a glass stir rod are used with a rubber gasket or rubber stopper to effect a seal during storage.

The components of the composition in parts by weight of the total composition are as follows:

Magnesium Usta:85–97%
Resublimated Iodine:1–3%
Iodine Crystals:0.5–1.5%
Iodine Powder:2–4%

The resublimated iodine may be obtained from Deepwater Chemical of Compton, Calif. Iodine crystals utilized were resublimated analytic reagent obtained from Mallinckrodt Chemical, St. Louis. Finally, the iodine powder used was a pure drug form obtained from S. B. Penick and Co., New York, N.Y.

The following is an example of a preferred formulation:

Using a glass container, Magnesium Usta was poured therein until the container was approximately ¾ full which quantity is equal to 95 parts per hundred of the total composition to be formulated. 1 and ½ parts resublimated iodine were then added to the Magnesium Usta and ¾ parts of iodine crystal was also added. The container was then tightly closed with a rubber gasket and covered for 48 hours. The container was then thoroughly shaken and 2.75 parts iodine powder added. A glass spatula was utilized to thoroughly stir the contents, and the container was sealed again for an additional 48 hours. After 48 hours, the container was thoroughly shaken and the composition of this invention was ready for packaging in for example, a polyethylene container.

In addition, to direct application of the above composition to wounds, abrasions, blisters, insect bites, and the like, the composition may be incorporated in a variety of different vehicles. The following examples are illustrative of the types of different vehicles, and these examples are intended to be illustrative only and not limitative of the scope of this invention.

Free Medicated Powder

A medicated powder dispensable from, for example, a plastic squeeze container or shake bottle, may be formulated in preferably a 5% concentration of the medicated composition of this invention in 95% pure talc. The medicated powder then will possess germicidal characteristics for when topically applied.

Ointment—Surgical Dressing

The composition of this invention may be incorporated in an ointment such as anhydrous lanolin in a 5–10% concentration. This ointment may be packaged in a tube or jar, as desired, and may be topically applied to boils, varicose-ulcers, cuts, burns, abrasions, blisters, and the like, with or without a dry bandage. The ointment in use does not irritate the affected area and application was not found to be accompanied by painful sensation.

Lotion

In the alternative, the medicinal composition of this invention may be formulated in a 5–10% concentration with a lotion vehicle. Any well known lotion vehicle may be utilized such as for example a vehicle consisting of 4 parts ethanol and 2 parts propylene glycol.

After Shave Lotion

A cosmetic after shave lotion having the medicinal composition of this invention present in for example about a 2% concentration may be formulated. The after shave vehicle containing the composition of this invention then is a soothing medicated formula for treatment of minor nicks and cuts. It may be packaged in a plastic squeeze bottle, as desired.

Cosmetic Make Up Stick

As in the case of the after shave lotion vehicle, the composition of this invention may also be incorporated in standard cosmetic make up bases such as make up sticks, cake or cream at preferably a 2% concentration. A medicated make up stick or the like, then in addition to its cosmetic functions, provides a medicated treatment for acne or other skin disorders.

Aerosol Bandage

The composition of this invention may also be incorporated in a spray-on aerosol bandage type formulation as a wound dressing. In a preferred embodiment thereof, the composition of this invention is incorporated in a concentration of 3.5 mg/g of the vehicle. A representative vehicle includes a copolymer of polyvinyl pyrrolidone and vinyl acetate present in the concentration of 16.7%, a plasticizer such as CITROFLEX obtainable from Pfizer & Co., Inc., Brooklyn, N.Y., 0.8% and anhydrox ethanol (200 proof) present in a concentration of 82.5%. The vehicle containing the composition of this invention is then incorporated in a standard propellent can. An example would be a 2¼ ounce Peerless aluminum can (Epon-lined with Precision NN Valve and standard spray actuator). Because the propellent is incompatible with the vehicle containing the composition of this invention, the vehicle mixture is separated from the propellant mixture. This separation necessitates a double valve aerosol spray apparatus. In the divided aerosol package the vehicle mixture occupies preferably 1/5 of the capacity and the propellent the remaining 4/5. Both the propellent and the can are obtainable commercially from a variety of different sources.

Test Results

An aerosol bandage formulation according to the example above was tested for stability at 43° C. for 6 months, and at ambient room temperature for 9 months. In each instance, the aerosol formulation was stored without loss of potency.

The composition of this invention, as well as the ointment and lotion formulations described above were applied to a wide variety of different types of cuts, burns, abrasions, blisters, boils, insect bites, acne, ulcerative-type lesions in humans. In each instance, application was not accompanied by a stinging or painful sensation to the patient, or in fact by any discomfort. In each instance the application was followed by rapid and complete healing with little or no infection observed.

Accordingly, this invention comprises a new and non-irritating medicinal composition including a mixture of magnesium and iodine which may be applied in powder form, or may be admixed with a cosmetic or pharmacological acceptable vehicle such as an ointment, lotion, or aerosol bandage. Preferably, the composition of this invention comprises from 85–97% magnesium with the remainder iodine, and the composition is formulated preferably with 95% Magnesium Usta, 1½% resublimated iodine, ¾% iodine crystals, and 2¾% iodine powder.

While the composition may be incorporated in cosmetic vehicles, in a preferred version, the cosmetic vehicles contain from about 2 to about 5% of the composition of this invention. When incorporated in ointment or lotion for topical application to wounds, abrasions, burns and the like, it preferably is present in a concentration of from 5–10%, by weight. It will be obvious to those skilled in the art, however, that the composition of this invention may be incorporated in a wide variety of well-known types of vehicles, and those disclosed herein are not intended to limit the scope of this invention.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are, therefore intended to be embraced therein.

We claim:

1. A non-irritating antiseptic composition for topical application to the human skin comprising a germicidally effective amount of a mixture prepared by mixing from about 85 to 97 parts magnesium usta and from 3½ to 8½ parts iodine and a pharmacologically or cosmetically acceptable vehicle.

2. The composition of claim 1, wherein said mixture further comprises about 95 parts Magnesium Usta and about 5 parts iodine.

3. The composition of claim 1, wherein said mixture is present in said vehicle in a concentration of from about 2 to about 10 percent by weight.

4. A method for providing germicidal protection against infection to preselected portions of the human body comprising:
   topically applying to said preselected portions, a germicidally effective amount of a composition of from about 2 to about 10 percent by weight of a mixture prepared by mixing 85 to 97 parts magnesium usta and 3½ to 8½ parts iodine in a pharmacologically or cosmetically acceptable vehicle.

5. The method of claim 4 wherein said mixture comprises about 95 parts magnesium usta in about 5 parts iodine.

6. The method of claim 4, wherein said vehicle comprises lanolin.

7. The method of claim 4, wherein said vehicle includes ethanol.

8. The method of claim 4, wherein said vehicle comprises talc.

* * * * *